United States Patent [19]
Jacobsen et al.

[11] Patent Number: 5,916,194
[45] Date of Patent: Jun. 29, 1999

[54] CATHETER/GUIDE WIRE STEERING APPARATUS AND METHOD

[75] Inventors: Stephen C. Jacobsen; John Lippert, both of Salt Lake City, Utah

[73] Assignee: Sarcos, Inc., Salt Lake City, Utah

[21] Appl. No.: 08/653,291

[22] Filed: May 24, 1996

[51] Int. Cl.⁶ .................................................. A61M 29/00
[52] U.S. Cl. .......................... 604/96; 606/194; 604/280
[58] Field of Search ............... 604/96–102, 264, 604/280; 600/192, 194

[56] References Cited

U.S. PATENT DOCUMENTS

| | | |
|---|---|---|
| 4,545,390 | 10/1985 | Leary . |
| 4,552,554 | 11/1985 | Gould et al. .............................. 604/51 |
| 4,884,579 | 12/1989 | Engelson . |
| 4,905,667 | 3/1990 | Foerster et al. ............................ 128/4 |
| 4,955,862 | 9/1990 | Sepetka . |
| 4,989,608 | 2/1991 | Ratner . |
| 4,994,069 | 2/1991 | Ritchart et al. . |
| 5,095,915 | 3/1992 | Engelson . |
| 5,116,305 | 5/1992 | Milder et al. ............................. 600/18 |
| 5,282,785 | 2/1994 | Shapland et al. ......................... 604/21 |
| 5,306,252 | 4/1994 | Yutori et al. . |
| 5,376,084 | 12/1994 | Bacich et al. . |
| 5,411,476 | 5/1995 | Abrams et al. ........................... 604/95 |
| 5,413,557 | 5/1995 | Solar ........................................ 604/96 |
| 5,413,581 | 5/1995 | Goy ......................................... 606/194 |
| 5,437,288 | 8/1995 | Schwartz et al. . |
| 5,438,993 | 8/1995 | Lynch et al. . |
| 5,439,000 | 8/1995 | Gunderson et al. . |
| 5,441,483 | 8/1995 | Avitall . |
| 5,441,489 | 8/1995 | Utsumi et al. . |
| 5,460,187 | 10/1995 | Daigle et al. . |
| 5,464,395 | 11/1995 | Faxon et al. .............................. 604/96 |
| 5,477,856 | 12/1995 | Lundquist . |
| 5,520,645 | 5/1996 | Imran et al. . |

FOREIGN PATENT DOCUMENTS 25 39191   10/1975   Germany .

*Primary Examiner*—Wynn Wood Coggins
*Assistant Examiner*—Deborah Blyveis
*Attorney, Agent, or Firm*—Thorpe, North & Western, L.L.P.

[57] ABSTRACT

A catheter/guide wire steering mechanism includes a catheter having a proximal end, a distal end, and sidewalls which define at least the first lumen. An opening is formed in a sidewall of the catheter, near the distal end thereof in communication with the first lumen. A plug is disposed in the catheter at the distal end thereof and includes a curved surface for deflecting and directing out the opening, the leading end of a guide wire (or other catheter) inserted into the lumen at the proximal end of the catheter. This enables guiding the guide wire laterally from the catheter either into a passageway branching from the main passageway into which the catheter is inserted, or to perforate a sidewall of the main passageway.

22 Claims, 2 Drawing Sheets

CATHETER/GUIDE WIRE STEERING APPARATUS AND METHOD

BACKGROUND OF THE INVENTION

This invention relates to a side exit catheter through which a guide wire and/or another catheter may be steered laterally of the catheter.

Catheter guide wires have been used for many years to guide catheters to desired target locations in the human bodies vasculature. Typical guide wires are from about 155 centimeters to 195 centimeters in length and are made of stainless steel, with a platinum alloy coil spring soldered or otherwise attached to the stainless steel wire at the distal end. The use of platinum for the coil spring provides radiopacity for X-ray viewing during navigation of the guide wire in the body and the coil spring reduces likelihood of puncture by the guide wire. Of course, other soft tips may be used for the leading end of the guide wire, the purpose being to reduce the likelihood of puncture of the anatomy.

Navigation through the anatomy is typically achieved by viewing the guide wire in the body using X-ray fluoroscopy. The guide wire is inserted into a vessel or duct (along with the catheter if desired) and moved therethrough until the guide wire tip reaches the desired vessel or duct branch. The proximal end of the guide wire is then rotated or torqued hopefully to a point where a curved tip of the guide wire is pointed toward the desired branch for advancement into the branch. The guide wire, with the catheter threaded thereover, are then advanced further until the tip of the guide wire reaches the target location. The catheter is then moved to the target location, following the guide wire. Once the catheter is in place, the guide wire may be withdrawn, depending upon the therapy to be performed.

If a vessel or duct branch extends from the main vessel or duct at an especially sharp angle, it becomes very difficult and in many cases impossible to simply rotate the curved tip of the guide wire so as to allow advancement of the tip into the branch. Of course, it would be desirable to provide apparatus for easily accommodating the movement of guide wires into angled branches of a vessel or duct and into other tortuous and twisting vasculature passageways.

SUMMARY OF THE INVENTION

It is an object of the invention to provide an improved apparatus and method for steering a guide wire and/or catheter through vasculature passageways.

It is also an object of the invention to provide such apparatus and method which allows for directing a guide wire into vessels or ducts which branch off from primary vessels or ducts at sharp angles.

It is a further object of the invention to provide such apparatus and method in which guide wires can be guided into branch vessels or ducts at angles up to 135 degrees and beyond.

It is another object of the invention to provide such apparatus which is simple in design and construction.

It is still a further object of the invention to provide such a method which is relatively easy to carry out.

It is also an object of the invention to provide such apparatus and method which allows for side exit from a vessel or duct, and entry via piercing into other tissue or other ducts.

The above and other objects of the invention are realized in a specific illustrative embodiment of a catheter/guide wire steering apparatus which includes a catheter having a proximal end, a distal end, and the sidewalls which define at least one lumen, an opening in a sidewall of the catheter, near the distal end thereof, in communication with the lumen, and a deflection element disposed in the catheter at the distal end thereof for deflecting and directing out the opening, the leading end of the guide wire inserted into the lumen at the proximal end of the catheter, to thereby enable guiding the guide wire laterally from the catheter.

In accordance with one aspect of the invention, the catheter includes a second lumen extending the length of the catheter for receiving a second guide wire to guide the catheter to a target location in a vasculature passageway. Also, an inflatable balloon is disposed at the distal end of the second lumen for expanding when contrast agent and/or saline solution or other liquid is forced into the second lumen, to force the opening in the first lumen against a sidewall of a vasculature or duct passageway into which the catheter is inserted. In this position, a guide wire may be inserted in the first lumen either to pierce the vasculature passageway sidewall or to travel into a branch duct branching from the vasculature passageway at the location of the first lumen opening.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Figure 1:
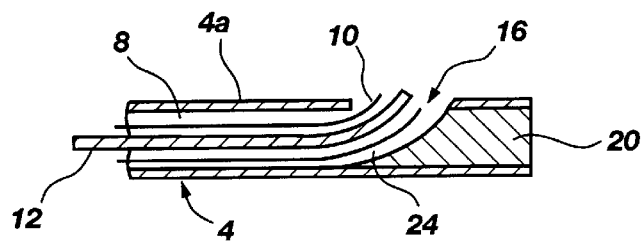
FIG. 1 is a side, fragmented, cross-sectional view of a catheter/guide wire steering apparatus made in accordance with the principles of the present invention.

Referring to FIG. 1, there is shown a side, fragmented, cross-sectional view of the distal end of a catheter 4 having a lumen 8, into which is threaded a smaller catheter 10, inside of which is a guide wire 12. An opening 16 is formed in a sidewall 4a of the catheter 4, for communication with the lumen 8. A plug 20 is disposed in the end of the catheter 4 and includes a gradually curving surface 24 formed on the sidewall of the catheter 4 opposite the opening 16, to deflect and direct both the smaller catheter 10 and the tip of the guide wire 12 laterally out of the opening 16. The plug 20, advantageously, is a radiopaque and lubricous polymer for ease of X-ray visualization and entry and exit. (A radiopaque band could also be used, as well as an MRI detectable plug or band for viewing during MRI procedures.)

In the manner described, a guide wire can be deflected and directed laterally from a catheter to a branch vessel or duct. This is accomplished by first threading the catheter through a vasculature passageway until the opening 16 is positioned adjacent a branch vessel or duct into which the guide wire 12 (and smaller catheter 10) is to be directed. Then, the guide wire 12 and smaller catheter 10 would be threaded through the catheter 4 until the leading tip of the guide wire 12 exited the opening 16 and entered the branch vessel or duct. The guide wire 12 could then be moved further to the desired target location, along with the smaller catheter 10.

Alternatively, the catheter 4 and guide wire 12 could be utilized without the catheter 10, to direct the guide wire into the branch vessel or duct. Then, the catheter 4 could be removed and catheter 10 threaded over the guide wire 12 to the desired location in the branch vessel or duct.

For the configuration shown in FIG. 1, the lumen 8 could advantageously have a diameter of from about 0.008 inches (for example, if guide wire only is to be inserted therein) to 0.078 inches (for example, if catheter and guide wire are to be inserted therein)—two preferred diameters being 0.020 inches and 0.042 inches, respectively. The exterior diameter of the catheter 10 could advantageously be from about 0.012 inches to 0.074 inches, with a preferred diameter being 0.038 inches, with the lumen of the catheter 10 being from about 0.008 inches to 0.065 inches in diameter, with a preferred diameter being 0.020 inches.

Figure 2:
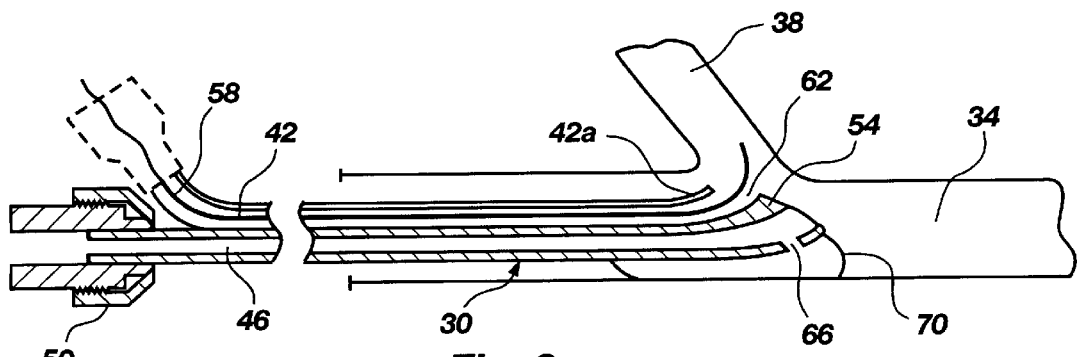
FIG. 2 is a side, fragmented, cross-sectional view of another embodiment of catheter/guide wire steering apparatus, also made in accordance with the principles of the present invention.

FIG. 2 shows a side, fragmented, cross-sectional view of a two-lumen catheter 30 made in accordance with the present invention. The catheter 30 is shown partially inserted into a body duct 34 having a branch duct 38.

The catheter 30 includes two lumens 42 and 46, with lumen 46 extending rearwardly a greater distance than lumen 42 and about which a torquing chuck 50 (and luer adapter) is disposed. (Of course, the torquing chuck 50 could be placed distally ahead of the branching of the lumens 42 and 46.) Formed in the distal end of the lumen 42 is a deflecting end wall 54 which is shaped similar to the plug 20 of FIG. 1, to deflect and direct a guide wire 58 inserted in the lumen 42 out of a side opening 62 of the catheter 30. A longitudinal slit (not shown) in the wall of lumen 42 could be provided to allow "change out" of the guide wire 58.

Coupled at the distal end of the catheter 30 to communicate through an opening 66 with the lumen 46 is a balloon 70. The balloon 70 is located on the opposite side of the catheter 30 from the opening 62 so that when inflated, it would tend to force the opening 62 toward the opposite wall of the duct 34 and, in this case, toward the branch duct 38. Thus, when the catheter 30 were threaded to the desired location in the duct 34, adjacent the branch duct 38, the balloon 70 would be inflated through the lumen 46 to cause the distal end of the catheter 30 to deflect or bend towards the branch duct 38. (If greater bending or deflection of the catheter 30 is desired, the balloon 70 and lumen 46 could be moved or extended more forwardly of lumen opening 62 so that greater pivoting and thus deflection of the distal end of the lumen 42 is achieved. Also, tapering the balloon 70 to be larger forwardly of the opening 62, increases the deflection angle.) This bending, along with a preformed curve 42a formed in the distal end of the catheter 30, and deflecting end wall 54, all serve to position the opening 62 against the opening to the branch duct 38 so that when the guide wire 58 is inserted into the lumen 42, the leading end of the guide wire will emerge from the opening 62 and move into the branch duct 38. The inflation of the balloon 70 may be adapted to occlude, in vessel 34, the flow of blood and medication or agents (particles, etc.) which may have been injected into the blood stream purposely or accidentally, or may be adapted to specifically not occlude.

Advantageously, balloon 70 may be made of a plastic material such as latex or, if greater rigidity is desired, it could be made of polyethylene, or similar plastic material.

A third lumen could be formed in the catheter 30 and used to initially thread the catheter to the desired location adjacent the branch duct 38 by threading this third lumen over a guide wire (not shown) which had been previously inserted in the main duct 34. However, if the primary vessel or duct 34 is large, or otherwise easily accessible, the catheter 30, with guide wire 58 partially threaded in lumen 42 and/or a guide wire partially threaded in lumen 46 may provide sufficient stiffness to allow insertion and guidance to the desired location. Also, a guide wire (not shown) partially inserted into lumen 46 may also suffice.

Advantageously, the diameter of lumen 42 is from about 0.008 inches to 0.078 inches and the diameter of lumen 46 is from about 0.012 inches to 0.040 inches. As in the FIG. 1 embodiment, a catheter could be used along with, i.e. threaded over, the guide wire 58.

Figure 3:
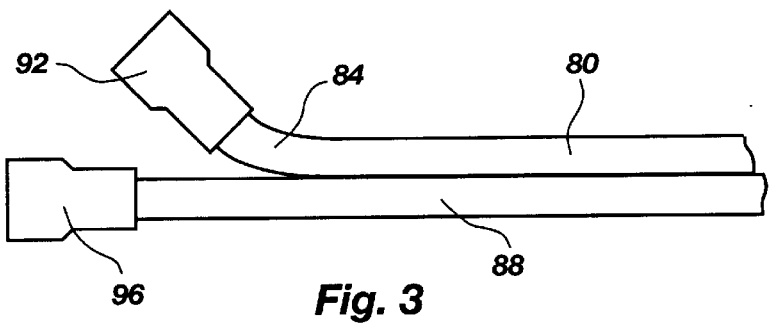
FIG. 3 is a side, fragmented view of the proximal end of a catheter, with luer adapters, in accordance with the present invention.

FIG. 3 shows the proximal end of a two-lumen catheter 80 in which one of the lumens 84 is flared laterally from the other lumen 88 to allow for more convenient access to the lumen 84. Disposed on the proximal ends of each of the lumens are luer adapters 92 and 96 for attaching medication supply devices and the like.

Figure 4:
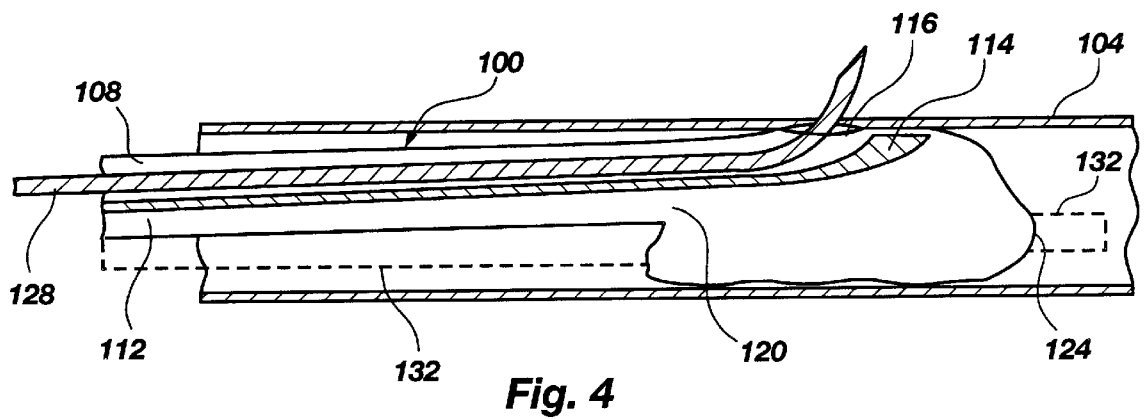
FIG. 4 is a side, fragmented, cross-sectional view of a catheter/guide wire steering apparatus, especially suitable for sidewall puncture of a body duct or passageway.
Figure 5:
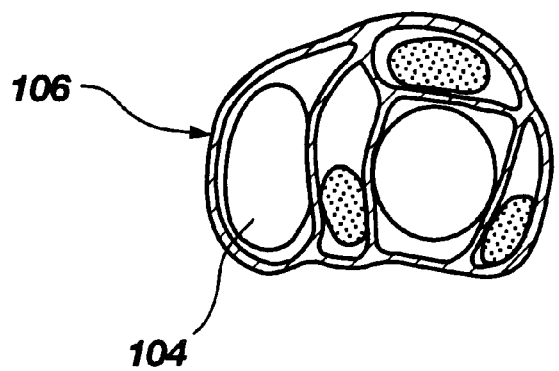
FIG. 5 is an end cross-sectional view of a nerve sheath.

FIG. 4 shows a side, fragmented, cross-sectional view of another two-lumen catheter 100, inserted in a vein 104, carried by a nerve sheath 106 (shown in cross-sectional view in FIG. 5). The object of the use of catheter 100 is to allow puncture of a wall of the vein 104 to allow introduction of anesthesia or other medication into the nerve sheath 106, without puncturing or damaging arteries or nerves also contained within the nerve sheath.

The catheter 100 includes two lumens 108 and 112, with the lumen 108 curved (using a deflecting end wall 114) at the distal end to exit through a side opening 116 formed in the catheter 100. Coupled over the distal end and opening 120 of the lumen 112 is a balloon 124 which, similarly to the arrangement of FIG. 2, when inflated forces the opening 116 against a sidewall of the vein 104. Inflation of the balloon 124 also serves to occlude the vein 104 and this aids in slowing the return of inadvertently injected medication to the heart. Varying the position of the balloon 124 relative to the opening 116 serves to vary the deflectability of the distal end of the catheter 100, as discussed earlier.

The catheter 100 is inserted in the vein 104 to the desired location and then when the balloon 124 is inflated to force the opening 116 against the sidewall of the vein, a perforating guide wire 128 is inserted in the lumen 108 and out the opening 116 to puncture the sidewall of the vein 104. Medication such as anesthesia would then be supplied through lumen 108 to flow through the perforation in the sidewall of the vein 104 into the nerve sheath, for example. Alternatively, guide wire 128 could be a laterally flexible "needle" or cannula, and the medication could be delivered through that.

With the configuration of FIG. 4, a third lumen (shown by dotted line 132) might be provided to allow introduction of medication into the vein 104 distal to the occluder balloon 124 to thus provide systemic blood access.

The diameter of the lumen 108 might advantageously be from about 0.008 inches to 0.042 inches, the diameter of lumen 112 might advantageously be from about 0.008 inches to 0.018 inches, and the diameter of lumen 132 might advantageously be from about 0.010 inches to 0.080 inches.

Figure 6:
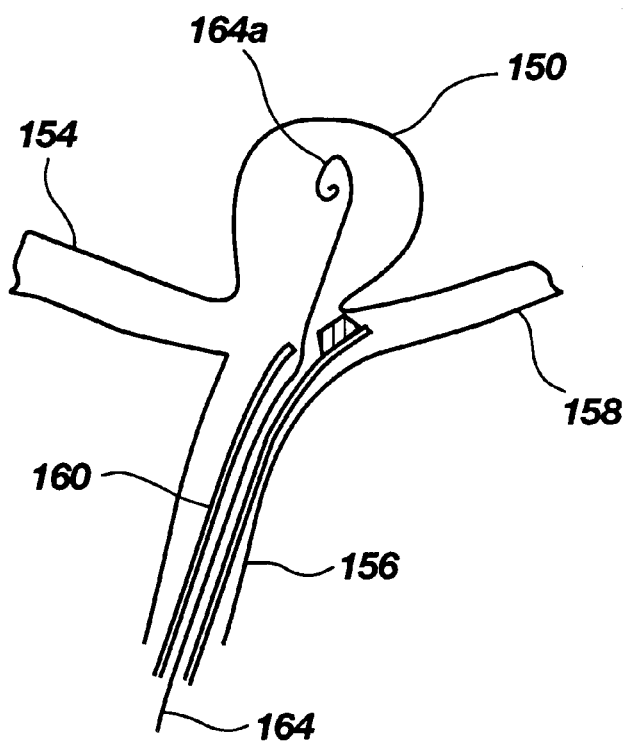
FIG. 6 is a side, fragmented, cross-sectional view of a catheter/guide wire steering apparatus, especially suitable for treatment of aneurysms.

FIG. 6 shows another use of a side exit catheter in a situation where an aneurysm 150 has developed at the intersection of three vessels 154, 156 and 158. A side exit catheter 160, as previously described, is inserted in vessel 156 until the tip and the exit opening are disposed at the intersection of the vessels, with the opening generally facing the aneurism 150, and the distal end of the catheter 160 safely resting in vessel 158 (or vessel 154 if the catheter is curved in the opposite direction). A wire 164 with a coil 164a may then be inserted into the lumen of the catheter and threaded upwardly, out the side exit opening and into the aneurysm 150. This allows access to the aneurysm without threat of puncture by the catheter tip. The side exit can now be used to deploy coils or other devices or agents into the aneurysms.

In FIG. 6, catheter 160 could be provided with an occlusion-type balloon, as previously discussed, so that when inflated, it would occlude vessel 158 or vessel 154 while treating the aneurysm. Also, two balloon catheters could be used so that both vessels 154 and 158 could be occluded while the treatment process proceeded. Such occlusion would protect against embolic or other materials traveling down the vessels during treatment. An additional lumen could be provided in catheter 160 to thereby allow supply of blood beyond the occlusion from vessel 156 to vessel 158 and/or vessel 154.

In the manner described, side-exit catheters may be provided to direct guide wires laterally into side branching ducts or passageways, to allow for perforating a sidewall of a duct or passageway into which the catheter is inserted, or to provide safe access into anatomy such as aneurysms.

To reduce resistance to movement of the catheters discussed above in a vasculature passageway, the surface of the catheters may be coated with a lubricous coating such as silicone-based oil and/or polymer or hydrophilic polymers. Lubricious coatings could also be applied to the lumens of the catheters to reduce resistance to movement of guide wires or other catheters therein.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. Catheter/guide wire steering apparatus for directing the catheter/guide wire to a desired location comprising:
   a catheter having a proximal end, a distal end, and sidewalls which define at least a first lumen,
   an opening in a sidewall of the catheter, near the distal end thereof, in communication with the lumen,
   means disposed in the catheter at the distal end thereof for deflecting and directing out the opening, the leading end of a guide wire or catheter, to thereby enable guiding the guide wire laterally from the catheter; and
   balloon means disposed on the distal end of the catheter, the balloon means being disposed so as to cause the distal end of the catheter to bend toward the desired location.

2. Apparatus as in claim 1 wherein the distal end of the catheter is shapeable to curve in the direction in which the opening faces.

3. Apparatus as in claim 1 further including a guide wire for insertion into the lumen at the proximal end of the catheter and exit out the opening thereof, said guide wire having a distal end which is curved laterally.

4. Apparatus as in claim 1 wherein said catheter includes a second lumen extending the length of the catheter for expanding the balloon means when liquid is forced into the second lumen, to deflect and force said opening against a sidewall of a vasculature/duct passageway into which the catheter is inserted.

5. Apparatus as in claim 4 wherein said catheter includes a third lumen extending from the proximal end of the catheter to the distal end thereof, beyond the location of the balloon means.

6. Apparatus as in claim 1 wherein said catheter includes a second lumen extending the length of the catheter for receiving a second guide wire to guide the catheter to a target location in a vasculature passageway.

7. Apparatus as in claim 6 wherein the second lumen includes an access opening at the proximal end of the catheter, and wherein the first lumen includes an access opening at the proximal end of the catheter nearer the distal end than the access opening of the second lumen.

8. Apparatus as in claim 7 wherein the access opening of the first lumen includes a luer adapter.

9. Apparatus as in claim 7 further including a torquing chuck disposed about the second lumen.

10. Apparatus as in claim 7 further including a torquing chuck disposed about the first and second lumens.

11. Apparatus as in claim 6 wherein the first lumen has a diameter of from about 0.008 inches to 0.078 inches, and wherein the second lumen has a diameter of from about 0.012 inches to 0.040 inches.

12. Apparatus as in claim 1 further including a radiopaque element disposed at the distal end of the catheter.

13. Apparatus as in claim 1 further including an element disposed at the distal end of the catheter made of a material detectable by MRI.

14. Apparatus as in claim 1 further including a lubricous coating disposed over the exterior of the catheter.

15. Apparatus as in claim 1 further including a lubricious coating disposed over the walls of the lumen.

16. Catheter/guide wire steering apparatus for directing the catheter/guide wire to a desired location comprising:
   a catheter having a proximal end, a distal end, and sidewalls which define at least a first lumen,
   an opening in a sidewall of the catheter, near the distal end thereof, in communication with the lumen,
   means disposed in the catheter at the distal end thereof for deflecting and directing out the opening, the leading end of a guide wire or catheter, to thereby enable guiding the guide wire laterally from the catheter; and
   balloon means disposed on the distal end of the catheter, the balloon means being disposed so that a greater portion of the balloon is disposed distally of the opening to thereby cause the distal end of the catheter to bend toward the desired location when the balloon is inflated.

17. A method of steering a catheter/guide wire in a vasculature passageway comprising the step of
   providing a catheter having a proximal end, a distal end, sidewalls which define at least a first lumen, and an opening in a sidewall near the distal end thereof, in communication with the lumen,
   providing a deflecting means in the catheter at a distal end thereof to deflect and direct out the opening the leading end of a guide wire or catheter inserted into the lumen at the proximal end of the catheter,
   providing a balloon which is positioned so as to bend the distal end of the catheter when the balloon is inflated, and inserting a catheter or guide wire into the lumen at the proximal end of the catheter to deflect the leading end of the catheter or guide wire out the opening.

18. Apparatus as in claim 1 wherein the balloon is disposed forwardly of the opening so as to increase deflection of the distal end of the lumen.

19. Apparatus as in claim 1 wherein the balloon is tapered to be larger forwardly of the opening to thereby increase deflection when the balloon is inflated.

20. The method according to claim 17, wherein the method comprises, more specifically, selectively placing the balloon with respect to the lumen so as to increase the bending of the lumen when the balloon is inflated.

21. The method according to claim 17, wherein the method comprises, more specifically, selecting a catheter having a balloon disposed on the distal tip thereof.

22. The method according to claim 17, wherein the method comprises, more specifically, selecting a catheter with a balloon which is larger distally of the opening.

* * * * *